United States Patent
Heidemann et al.

(12) 
(10) Patent No.: US 6,362,345 B1
(45) Date of Patent: Mar. 26, 2002

(54) METHOD FOR PRODUCING PHTHALIC ANHYDRIDE BY MEANS OF CATALYTIC VAPOR-PHASE OXIDATION OF O-XYLOL/NAPHTHALENE MIXTURES

(75) Inventors: Thomas Heidemann, Weinheim; Heiko Arnold, Mannheim; Gerhard Hefele, Römerberg; Herbert Wanjek, Maxdorf, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/700,427

(22) PCT Filed: May 10, 1999

(86) PCT No.: PCT/EP99/03192

§ 371 Date: Nov. 15, 2000

§ 102(e) Date: Nov. 15, 2000

(87) PCT Pub. No.: WO99/61434

PCT Pub. Date: Dec. 2, 1999

(30) Foreign Application Priority Data

May 26, 1998 (DE) .......................... 198 23 275

(51) Int. Cl.[7] ............................................ C07D 307/89
(52) U.S. Cl. ........................................... 549/248
(58) Field of Search ................................ 549/248

(56) References Cited

U.S. PATENT DOCUMENTS

| | | | |
|---|---|---|---|
| 3,394,468 A | 7/1968 | Zeller | 34/57 |
| 3,565,829 A | 2/1971 | Friedrichsen | 252/464 |
| 3,684,741 A | 8/1972 | Friedrichsen | 252/435 |
| 3,799,886 A | 3/1974 | Felice | 252/461 |
| 3,898,249 A | 8/1975 | Felice | 260/366.4 |
| 4,046,780 A | 9/1977 | Nakanishi | 260/346.4 |
| 4,472,587 A | 9/1984 | Benedetti | 549/428 |
| 5,677,261 A | 10/1997 | Tenten | 502/439 |
| 5,792,719 A | 8/1998 | Eberle | 502/178 |

FOREIGN PATENT DOCUMENTS

| | | |
|---|---|---|
| DE | 1 280 756 | 4/1970 |
| DE | 1 642 938 | 5/1971 |
| DE | 1 769 998 | 2/1972 |
| DE | 2 106 796 | 8/1972 |
| DE | 22 38 067 | 2/1974 |
| EP | 286 448 | 10/1988 |
| EP | 539 878 | 5/1993 |
| EP | 714 700 | 6/1996 |
| EP | 744 214 | 11/1996 |
| WO | 98/37965 | 9/1989 |
| WO | 98/37967 | 9/1998 |

Primary Examiner—Floyd D. Higel
Assistant Examiner—Andrea D'Souza Small
(74) Attorney, Agent, or Firm—Keil & Weinkauf

(57) ABSTRACT

In a process for preparing phthalic anhydride by catalytic gas-phase oxidation of o-xylene/naphthalene mixtures by molecular oxygen, use is made of a catalyst I in a first zone on the gas inlet side which makes up from 25 to 75 percent by volume of the total catalyst volume, comprising, in each case based on the catalytically active composition, from 1 to 10% by weight of vanadium oxide (calculated as $V_2O_5$), from 1 to 10% by weight of antimony oxide (calculated as $Sb_2O_3$) and from 80 to 98% by weight of titanium dioxide of the anatase type having a BET surface area of from 13 to 28 $m^2/g$ and also from 0.05 to 1% by weight of cesium (calculated as Cs) applied to a steatite support and a catalyst II in a second zone which makes up the remaining 75 to 25 percent by volume of the total catalyst volume, comprising, in each case based on the catalytically active composition, from 1 to 10% by weight of vanadium oxide (calculated as $V_2O_5$), from 1 to 10% by weight of antimony oxide (calculated as $Sb_2O_3$) and from 80 to 98% by weight of titanium dioxide of the anatase type having a BET surface area of from 13 to 28 $m^2/g$ and from 0.01 to 1% by weight of phosphorus oxide (calculated as P) and also from 0.01 to 0.2% by weight of cesium (calculated as Cs) applied to a steatite support, wherein the cesium content of the catalyst II is less than 15% by weight of the cesium content of the catalyst I and the catalyst I and the catalyst II have been prepared without addition of compounds of niobium.

8 Claims, No Drawings

METHOD FOR PRODUCING PHTHALIC ANHYDRIDE BY MEANS OF CATALYTIC VAPOR-PHASE OXIDATION OF O-XYLOL/ NAPHTHALENE MIXTURES

This application is a 371 of PCT/EP99/03192 May 10, 1999.

The present invention relates to a process for preparing phthalic anhydride by catalytic gas-phase oxidation of o-xylene/naphthalene mixtures by molecular oxygen using 2 catalyst beds comprising coated catalysts which comprise cesium, where the cesium content of the catalyst of the second zone is less than 15% by weight of the cesium content of the first zone.

The gas-phase oxidation of o-xylene and/or naphthalene to give phthalic anhydride is well known and has been widely described in the literature. It is generally carried out by passing a mixture of a gas comprising molecular oxygen, for example air, and the starting material to be oxidized through a multiplicity of tubes arranged in a reactor, with a bed of at least one catalyst being located in the tubes. To regulate the temperature, the tubes are surrounded by a heat transfer medium, for example a salt melt. Despite this thermostating, it is possible for "hot spots" in which the temperature is higher than in the remainder of the catalyst bed to occur. These hot spots give rise to secondary reactions such as the total combustion of the starting material or they lead to the formation of undesirable by-products which can be separated from the reaction product only with great difficulty, if at all, for example the formation of phthalide or naphthoquinone. To weaken these hot spots, it has already been proposed that catalysts of different activity be arranged in zones in the catalyst bed, with the less active catalyst generally being arranged toward the gas inlet end and the more active catalyst being arranged toward the gas outlet from the catalyst bed. The catalysts of different activity in the catalyst bed can be exposed to the reaction gas at the same temperature, but the two zones of catalysts of different activity can also be thermostated to different reaction temperatures for contact with the reaction gas.

Catalysts which have been proven useful for the preparation of phthalic anhydride are coated catalysts (see below).

The oxidation of naphthalene or o-xylene is, owing to the different reactivities of the starting materials, generally carried out using different catalysts, so that when o-xylene/naphthalene mixtures are employed, it is necessary to use specifically adapted-catalysts which are suitable both for the oxidation of o-xylene and the oxidation of naphthalene, as is described, for example, in BE 893521, EP 286448 and DE 2238067.

A specific solution to this problem is proposed in EP 539878, which states that, when using catalysts of the inlet stage in a bed height of 15–85%, based on the volume of the total catalyst bed, and a catalyst of the subsequent stage in a bed height of 85–15%, based on the volume of the total catalyst bed, in the direction of the gas outlet, in the form of superposed zones, very good results are achieved when, in the catalyst of the inlet stage, a catalyst substance is applied to an inactive support in a ratio in the range from 5 to 20 g/100 ml, where the catalytically active substance comprises from 1 to 20% by weight of $V_2O_5$ and from 99 to 80% by weight of titanium dioxide of the anatase type having a specific surface area of from 10 to 60 $m^2/g$, with incorporation of, based on 100 parts by weight of the total amount of the abovementioned two components, from 0.01 to 1% by weight of $Nb_2O_5$, from 0.2 to 1.2% by weight of $P_2O_5$, from 0.5 to 5% by weight of $Sb_2O_3$ and from 0.3 to 1.2% by weight of at least one compound selected from the group consisting of oxides of potassium, cesium, rubidium and thallium, where in the catalyst of the second zone the amount of a compound selected from the group consisting of compounds of potassium, cesium, rubidium and thallium is from 17 to 63% by weight of the amount of the corresponding compound in the catalyst of the inlet stage. Outside this "window" (variation of the length ratio of the second catalyst to the total length within the range 85–15% and the alkali metal ratio within the range 17–63%), the reaction is, according to this patent, "difficult" or associated with relatively high yield losses.

It is an object of the present invention to remedy these deficiencies.

We have found that this object is achieved by using catalysts of virtually the above composition in which the alkali metal present is cesium and the cesium content of the second zone is less than 15% by weight of the cesium content of the first zone. Such catalysts have particularly advantageous properties compared to the above-described catalysts in the specified "window".

Specifically, we have found an improved process for preparing phthalic anhydride by catalytic gas-phase oxidation of o-xylene/naphthalene mixtures by molecular oxygen using a catalyst I in a first zone on the gas inlet side which makes up from 25 to 75 percent by volume of the total catalyst volume, comprising, in each case based on the catalytically active composition, from 1 to 10% by weight of vanadium oxide (calculated as $V_2O_5$), from 1 to 10% by weight of antimony oxide (calculated as $Sb_2O_3$) and from 80 to 98% by weight of titanium dioxide of the anatase type having a BET surface area of from 13 to 28 $m^2/g$ and also from 0.05 to 1% by weight of cesium (calculated as Cs) applied to a steatite support and a catalyst II in a second zone which makes up the remaining 75 to 25 percent by volume of the total catalyst volume, comprising, in each case based on the catalytically active composition, from 1 to 10% by weight of vanadium oxide (calculated as $V_2O_5$), from 1 to 10% by weight of antimony oxide (calculated as $Sb_2O_3$) and from 80 to 98% by weight of titanium dioxide of the anatase type having a BET surface area (cf. J. Amer. Chem. Soc. 60 (1938), 309 et seq.) of from 13 to 28 $m^2/g$ and from 0.01 to 1% by weight of phosphorus oxide (calculated as P) and also from 0.01 to 0.2% by weight of cesium (calculated as Cs) applied to a steatite support, wherein the cesium content of the catalyst II is less than 15% by weight of the cesium content of the catalyst I and the catalyst I and the catalyst II have been prepared without addition of compounds of niobium.

The reduction of the cesium content of the catalyst II to less than 15% by weight of the cesium content of the catalyst I enables the product quality to be significantly increased by reducing the content of the undesirable by-products phthalide and naphthoquinone without significantly influencing the phthalic anhydride yield. This is especially pronounced at the relatively low bath temperatures which are necessary to achieve space velocities over the catalyst of more than 60 g/standard $m^3$. This effect is particularly noticeable when the cesium content of the catalyst II is 10–13% by weight of the cesium content of catalyst I and the proportion of the total catalyst bed occupied by the zone of the catalyst II is 40–60%.

The catalysts used can, even without doping, further comprise small amounts of metal oxides such as those of niobium, tungsten and/or lead. These arise via possible impurities in the commercial anatase used and should thus not be regarded as doping of active compositions. Further impurities, in particular alkali metal impurities, are generally less than 0.01% by weight.

Catalysts which can be used in the process of the present invention are, within the limits defined in the claims, coated catalysts known per se, as are described in the specialist literature for preparing phthalic anhydride. The composition and production of such "standard catalysts" can be summarized as follows:

in general, catalysts which have found to be useful are coated catalysts in which the catalytically active composition ("active composition") is applied in the form of a shell to a support material which is generally inert under the reaction conditions, e.g. quartz ($SiO_2$), porcelain, magnesium oxide, tin dioxide, silicon carbide, rutile, alumina ($Al_2O_3$), aluminum silicate, magnesium silicate (steatite), zirconium silicate or cerium silicate or mixtures thereof. The catalytically active constituents of the catalytically active composition of these coated catalysts are generally titanium dioxide in its anatase modification plus vanadium pentoxide. In addition, the catalytically active composition can further comprise small amounts of many other oxidic compounds which act as promoters to influence the activity and selectivity of the catalyst by reducing or increasing its activity. Examples of such promoters are the alkali metal oxides, in particular lithium, potassium, rubidium and cesium oxide, thallium(I) oxide, aluminum oxide, zirconium oxide, iron oxide, nickel oxide, cobalt oxide, manganese oxide, tin oxide, silver oxide, copper oxide, chromium oxide, molybdenum oxide, tungsten oxide, iridium oxide, tantalum oxide, niobium oxide, arsenic oxide, antimony oxide, cerium oxide and phosphorus pentoxide. Promoters which reduce the activity and increase the selectivity are, for example, the alkali metal oxides, whereas oxidic phosphorus compounds, in particular phosphorus pentoxide, increase the activity of the catalyst but reduce its selectivity.

Such coated catalysts are produced, according to the processes of DE-A 1642938 and DE-A 1769998, by spraying an aqueous and/or organic solvent-containing solution or suspension of the constituents of the active composition and/or their precursor compounds, hereinafter referred to as the "slurry", onto the support material in a heated coating drum at elevated temperature until the amount of active composition as a proportion by weight of the total catalyst has reached the desired value. According to DE 2106796, the coating procedure can also be carried out in fluidized-bed coaters as are described, for example, in DE 1280756. However, both spraying in the coating drum and coating in a fluidized bed result in high losses since considerable amounts of the slurry are converted into a mist or parts of the previously applied active composition are rubbed off again by abrasion and are carried out by the waste gas. The proportion of active composition in the total catalyst should generally only deviate slightly from the specified value, because the amount of active composition applied and thus the thickness of the coating considerably influence activity and selectivity of the catalyst. Thus, the catalyst has, in the production methods indicated, to be cooled, taken from the coating drum or the fluidized bed and reweighed at frequent intervals to determine the amount of active composition applied. If too much active composition is deposited on the catalyst support, subsequent, careful removal of the excess active composition is generally not possible without adversely affecting the strength of the shell, in particular without crack formation in the catalyst shell.

One way of reducing this problem, which has also been employed in industry, is to add organic binders, preferably copolymers of vinyl acetate/vinyl laurate, vinyl acetate/acrylate, styrene/acrylate, vinyl acetate/maleate or vinyl acetate/ethylene, advantageously in the form of an aqueous dispersion, to the slurry, using binder amounts of 10–20% by weight, based on the solids content of the slurry (EP-A 744214). If the slurry is applied to the support without organic binders, coating temperatures above 150° C. are advantageous. when the above-described binders are added, the usable coating temperatures are, depending on the binder used, from 50 to 450° C. (DE 2106796). The binders applied burn off within a short time after introducing the catalyst into the reactor and starting up the reactor. The addition of binder has the additional advantage that the active composition adheres well to the support so that transport and charging of the catalyst are made easier.

Further suitable methods of producing coated catalysts for the catalytic gas-phase oxidation of aromatic hydrocarbons to give carboxylic acids and/or carboxylic anhydrides are described in WO-98/00778 and EP-A 714700. The layer containing catalytically active metal oxides is applied to a support material by first preparing a powder from a solution and/or a suspension of the catalytically active metal oxides and/or their precursor compounds, if desired in the presence of auxiliaries for catalyst production, subsequently applying this to the support, if desired after prior conditioning or, if desired, after heat treatment to generate the catalytically active metal oxides, and subjecting the support which has been coated in this way to a heat treatment to generate the catalytically active metal oxides or a treatment to remove volatile constituents.

To carry out the gas-phase oxidation, the reaction tubes of the reactor, which are thermostated from the outside to the reaction temperature, for example by means of salt melts, are first charged with the catalysts. The reaction gas is passed over the prepared catalyst bed.

The reaction gas fed to the catalyst is generally produced by mixing a gas comprising molecular oxygen, which can further comprise suitable reaction moderators and/or diluents such as steam, carbon dioxide and/or nitrogen in addition to oxygen, with the aromatic hydrocarbon to be oxidized. The gas comprising the molecular oxygen generally comprises from 1 to 100 mol%, preferably from 2 to 50 mol % and particularly preferably from 10 to 30 mol %, of oxygen, from 0 to 30 mol %, preferably from 0 to 10 mol %, of steam and from 0 to 50 mol %, preferably from 0 to 1 mol %, of carbon dioxide and nitrogen as the balance. To produce the reaction gas, the aromatic hydrocarbon to be oxidized is generally introduced into the gas comprising the molecular oxygen in an amount of from 30 to 150 g per standard $m^3$ of gas.

The o-xylene/naphthalene mixture to be oxidized can be used in a broad mixing ratio, for example in a weight ratio of from 1:99 to 99:1, but especially in such a ratio that the o-xylene content is at least 30% by weight, preferably at least 50% by weight and in particular at least 70% by weight. The ratio of o-xylene/naphthalene can remain constant over the catalyst life or can be altered. Thus, for example, the content of o-xylene can advantageously be increased over the course of time, thereby achieving a higher yield.

The reaction is generally carried out at from 300 to 450° C., preferably from 320 to 420° C. and particularly preferably from 340 to 400° C., and at a gauge pressure of from 0.1 to 2.5 bar, preferably from 0.3 to 1.5 bar, using a space velocity of generally from 750 to 500 h$^{-1}$.

The preparation of phthalic anhydride over the coated catalysts to be used according to the present invention is otherwise carried out in a manner known per se, as described specifically, for example, by K. Towae, W. Enke, R. Jäckh and N. Bhargawa in "Phthalic Acid and Derivatives", Ullmann's Encyclopedia of Industrial Chemistry, Vol. A20, 1992, 181.

EXAMPLES

Example 1:
Production of catalyst I 700 g of steatite (magnesium silicate) in the form of rings having an external diameter of 8 mm, a height of 6 mm and a wall thickness of 1.5 mm were heated to 210° C. in a coating drum and sprayed with a suspension of 400.0 g of anatase having a BET surface area of 21 m$^2$/g, 57.6 g of vanadyl oxalate, 14.4 g of antimony trioxide, 2.5 g of ammonium hydrogen phosphate, 2.60 g of cesium sulfate, 618 g of water and 128 g of formamide until the weight of the applied layer was 10.5% of the total weight of the finished catalyst. The catalytically active composition applied in this way, i.e. the catalyst coating, comprised 0.15% by weight of phosphorus (calculated as P), 7.5% by weight of vanadium (calculated as V$_2$O$_5$), 3.2% by weight of antimony (calculated as Sb$_2$O$_3$), 0.4% by weight of cesium (calculated as Cs) and 88.75% by weight of titanium dioxide.

Example 2:
Production of catalyst II 700 g of steatite (magnesium silicate) rings having an external diameter of 8 mm, a height of 6 mm and a wall thickness of 1.5 mm were heated to 210° C. in a coating drum and sprayed with a suspension of 400.0 g of anatase having a BET surface area of 20 m$^2$/g, 57.6 g of vanadyl oxalate, 14.4 g of antimony trioxide, 2.5 g of ammonium hydrogen phosphate, 0.32 g of cesium sulfate, 618 g of water and 128 g of formamide until the weight of the applied layer was 10.5% of the total weight of the finished catalyst. The catalytically active composition applied in this way, i.e. the catalyst coating, comprised 0.15% by weight of phosphorus (calculated as P), 7.5% by weight of vanadium (calculated as V$_2$O$_5$), 3.2% by weight of antimony (calculated as Sb$_2$O$_3$), 0.05% by weight of cesium (calculated as Cs) and 89.1% by weight of titanium dioxide.

Example 3:
Production of a comparative catalyst 700 g of steatite (magnesium silicate) in the form of rings having an external diameter of 8 mm, a height of 6 mm and a wall thickness of 1.5 mm were heated to 210° C. in a coating drum and sprayed with a suspension of 400.0 g of anatase having a BET surface area of 20 m$^2$/g, 57.6 g of vanadyl oxalate, 14.4 g of antimony trioxide, 2.5 g of ammonium hydrogen phosphate, 0.65 g of cesium sulfate, 618 g of water and 128 g of formamide until the weight of the applied layer was 10.5% of the total weight of the finished catalyst. The catalytically active composition applied in this way, i.e. the catalyst coating, comprised 0.15% by weight of phosphorus (calculated as P), 7.5% by weight of vanadium (calculated as V$_2$O$_5$), 3.2% by weight of antimony (calculated as Sb$_2$O$_3$), 0.1% by weight of cesium (calculated as Cs) and 89.05% by weight of titanium dioxide.

Example 4:
Preparation of PA

An iron tube having a length of 3.85 m and an internal diameter of 25 mm was charged with 1.30 m of catalyst II or the comparative catalyst of Example 3 and subsequently with 1.60 m of catalyst I. The iron tube was surrounded by a salt melt to regulate the temperature; a 4 mm thermocouple sheath with withdrawable thermocouple was employed for measuring the temperature of the catalyst. 4.0 standard m$^3$/h of air with loadings of a mixture of 75% by weight of o-xylene and 25% by weight of naphthalene rising from 0 to about 80 g/standard m$^3$ of air were passed through the tube from the top downward. The further procedure and the results obtained were as follows:

a) The proportion by length of the total catalyst bed occupied by catalyst II was 45%. The cesium content of catalyst II was 12.5% by weight of the cesium content of catalyst I. Further experimental parameters and results

| Loading [g of mixture/ standard m$^3$ of air] | Bath temperature [° C.] | Average PA yield [% by weight] | Phthalide in crude PA [% by weight] | Naphthoquinone in crude PA [% by weight] |
|---|---|---|---|---|
| 65–80 | 357–354 | 110 | <0.2 | <0.15 | b) The proportion by length of the total catalyst bed occupied by the comparative catalyst was 45%. The cesium content of the comparative catalyst was 25% by weight of the cesium content of catalyst I. Further experimental parameters and results:

| Loading [g of mixture/ standard m$^3$ of air] | Bath temperature [° C.] | Average PA yield [% by weight] | Phthalide in crude PA [% by weight] | Naphthoquinone in crude PA [% by weight] |
|---|---|---|---|---|
| >65 | <357 | * | >0.2 | >0.2 |

*could not be run, since by-products too high

We claim:

1. A process for preparing phthalic anhydride by catalytic gas-phase oxidation of o-xylene/naphthalene mixtures by molecular oxygen using a catalyst I in a first zone on the gas inlet side which makes up from 25 to 75 percent by volume of the total catalyst volume, comprising, in each case based on the catalytically active composition, from 1 to 10% by weight of vanadium oxide (calculated as V$_2$O$_5$), from 1 to 10% by weight of antimony oxide (calculated as Sb$_2$O$_3$) and from 80 to 98% by weight of titanium dioxide of the anatase type having a BET surface area of from 13 to 28 m$^2$/g and also from 0.05 to 1% by weight of cesium (calculated as Cs) applied to a steatite support and a catalyst II in a second zone which makes up the remaining 75 to 25 percent by volume of the total catalyst volume, comprising, in each case based on the catalytically active composition, from 1 to 10% by weight of vanadium oxide (calculated as V$_2$O$_5$), from 1 to 10% by weight of antimony oxide (calculated as Sb$_2$O$_3$) and from 80 to 98% by weight of titanium oxide of the anatase type having a BET surface area of from 13 to 28 m$^2$/g and from 0.01 to 1% by weight of phosphorus oxide (calculated as P) and also from 0.01 to 0.2% by weight of cesium (calculated as Cs) applied to a steatite support, wherein the cesium content of the catalyst II is less than 15% by weight of the cesium content of the catalyst I and the catalyst I and the catalyst II have been prepared without addition of compounds of niobium.

2. A process as claimed in claim 1, wherein the catalyst I is used in the first 40 to 60 percent by volume of the catalyst volume in the flow direction of the mixture of o-xylene/naphthalene mixture and reaction gas and the catalyst II is used in the last 60 to 40 percent by volume of the catalyst volume.

3. A process as claimed in claim 1, wherein titanium dioxide of the anatase type having a BET surface area of from 19 to 21 m$^2$/g is used.

4. A process as claimed in claim 1, wherein the composition of the catalysts I and II is identical except for the cesium content.

5. A process as claimed in claim 1, wherein the cesium content of the catalyst II is from 10 to 13% by weight of the cesium content of the catalyst I.

6. A process as claimed in claim 1, wherein the o-xylene content of the mixture of the starting substances of o-xylene and naphthalene is at least 30% by weight.

7. A process as claimed in claim 1, wherein the o-xylene content of the mixture of the starting substances of o-xylene and naphthalene is at least 50% by weight.

8. A process as claimed in claim 1, wherein the o-xylene content of the mixture of the starting substances of o-xylene and naphthalene is at least 70% by weight.

* * * * *